United States Patent [19]
Jakubowicz et al.

[11] 4,302,420
[45] Nov. 24, 1981

[54] ANALYZER FEATURING A CONTACTING REFLECTOMETER

[75] Inventors: Raymond F. Jakubowicz, Rush; Paul N. Schnipelsky, Rochester, both of N.Y.

[73] Assignee: Eastman Kodak Company, Rochester, N.Y.

[21] Appl. No.: 223,559

[22] Filed: Jan. 9, 1981

[51] Int. Cl.³ .......................... G01N 1/28; G01N 35/04
[52] U.S. Cl. ....................................... 422/63; 356/244; 422/65
[58] Field of Search ....................... 422/63, 64, 65, 66; 356/244, 246

[56] References Cited
U.S. PATENT DOCUMENTS 3,526,480 9/1970 Findl et al. ............................ 422/66
3,932,133 1/1976 Ishikawa ........................... 422/66 X Primary Examiner—Ronald Serwin
Attorney, Agent, or Firm—Dana M. Schmidt

[57] ABSTRACT

In an analyzer of the kind in which a reflectometer contacts a test element during scanning of the element, means are provided for moving test elements to and from the reflectometer in a manner avoiding significant contact wear of the reflectometer.

14 Claims, 10 Drawing Figures

ANALYZER FEATURING A CONTACTING REFLECTOMETER

FIELD OF THE INVENTION

This invention relates to apparatus for the chemical analysis of substances, known as analytes, in liquids. More specifically, it relates to a reflectometer analyzer.

BACKGROUND OF THE INVENTION

Radiometric analyzers prior to this invention have featured photometers and reflectometers of various kinds, often used with an incubator, for detecting a radiometric change in a test element. Examples of analyzers are described in commonly owned U.S. Application Ser. No. 177,050, filed on Aug. 11, 1980, by Jessop, entitled "Analyzer Apparatus Featuring a Simplified Incubator," wherein means are provided for automatically moving the test element into and out of the reflectometer station.

One useful reflectometer is a fiber optics reflectometer having an optical scanning head comprising a light-emitting optical fiber and a light-collecting optical fiber. Such a scanning head gives optimal performance if it is pressed against the test element during scanning, to minimize light losses. However, if such a fiber optics reflectometer were to be used in an analyzer of the type described in the above-noted Jessop application, there would be constant wear on the optical scanning head when the test element is pushed off the head by the automatic feed mechanism, after being scanned. Such constant wear could be avoided by gearing and linkages which are activated to move the reflectometer out of contact with the element prior to movement of the test element out of the reflectometer station. However, such gearing mechanisms are too cumbersome and expensive. A simpler mechanism is needed to permit the use of a contacting reflectometer, such as the fiber optics reflectometer described above.

SUMMARY OF THE INVENTION

This invention is directed to apparatus that permits the use of an element-contacting reflectometer in an analyzer that also uses an automatic feeding mechanism, without incurring undue wear of the scanning head of the reflectometer.

More specifically, in one aspect of the invention there is provided an improved analyzer for measuring an analyte of a liquid in a test element. The analyzer includes a reflectometer having a face adapted to contact a test element during scanning and means for biasing the test element and the reflectometer face into contact while the element is being scanned. The analyzer improvement comprises removing means for removing a scanned test element from the reflectometer, the removing means including first means for moving the scanned element and the reflectometer face out of contact with each other, and second means for pushing the element across the face, the first means and the second means being configured and arranged so that the second means is operative only after the first means is operative.

In another aspect of the invention, the analyzer includes advancing means for moving a test element into scanning position within the reflectometer, and means for removing a scanned test element from the reflectometer, the removing means being provided with a camming surface at one end thereof. The camming surface is beveled at an angle sufficient to lift a test element off the scanning head and onto the removing means as the camming surface is advanced toward the scanning head. The advancing means and the removing means are coupled for synchronous movement.

Thus, an advantage of the present invention is that a fiber optics reflectometer can be used in an analyzer to contact the test element to be scanned, without creating undue wear on the scanning head of the reflectometer and without requiring complicated mechanisms to prevent wear.

A related advantage of this invention is the provision of an inexpensive analyzer such as can be used in doctors' offices.

Other features and advantages will become apparent upon reference to the following Description of the Preferred Embodiments when read in light of the attached drawings.

DESCRIPTION OF THE PREFERRED EMBODIMENTS

Figure 1:
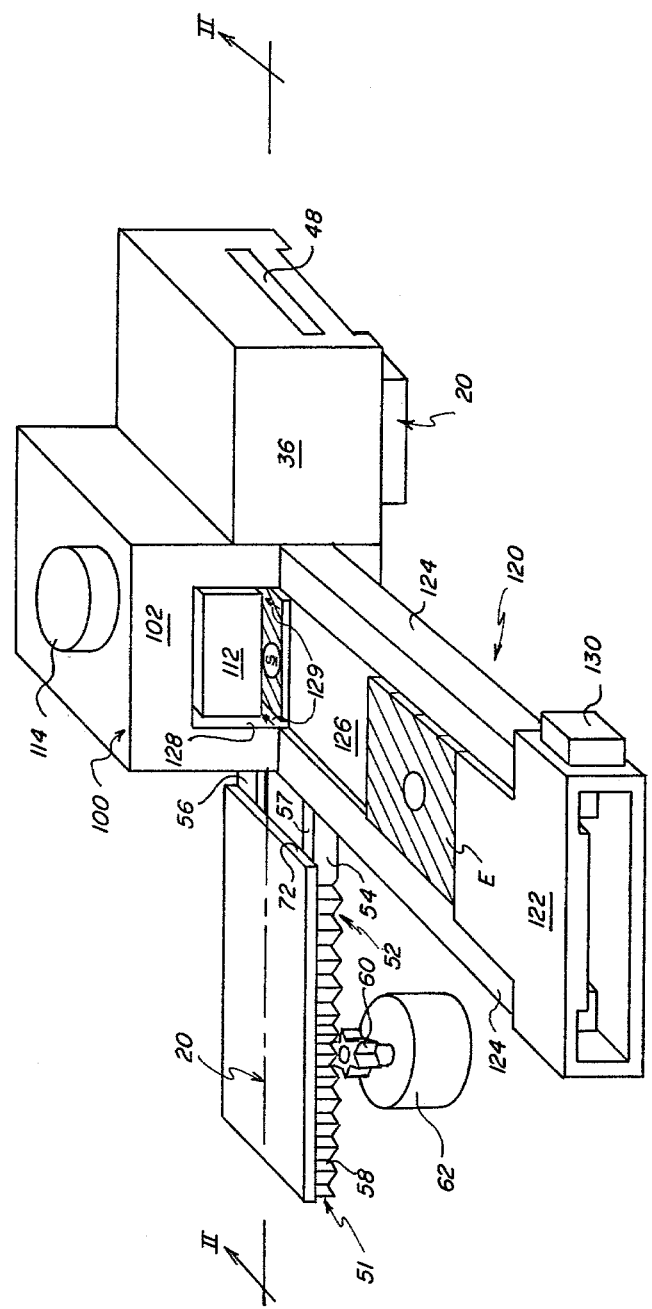
FIG. 1 is an isometric view of an analyzer constructed in accordance with the invention.

The specific embodiments hereinafter described refer to a fiber optics reflectometer as the preferred embodiment of this analyzer. In addition, the invention is applicable to an analyzer using any other reflectometer that scans a test element by contacting it. As used herein, "scan" refers to the act of intensely examining at least a portion of the test element in question by the use of electromagnetic energy, whether or not the object is examined a portion at a time in an ordered sequence.

The analyzer of this invention is capable of measuring a variety of analytes of liquids, particularly those of biological liquids. This is accomplished conveniently through the use of generally flat test elements E and E', FIG. 2, that feature one or more sample-containing portions mounted in a plastic frame member 15. The sample-containing portions are mounted on a transparent, liquid-impervious support 14. The sample is applied by depositing a quantity of liquid, such as a drop, onto the test element.

Edges 16 and 17 define the leading and trailing edges, respectively, of the elements as they are moved into the reflectometer.

The layers of the test elements preferably are constructed in the manner described in U.S. Pat. Nos. 3,992,158, issued Nov. 16, 1976, and 4,066,403, issued Jan. 3, 1978, the details of which are expressly incorporated herein by reference. Deposited liquid spreads into the layers where the reaction takes place that generates a detectable change. U.S. Pat. No. 4,169,751, issued on Oct. 2, 1979, discloses one useful form of such a test element wherein the sample-receiving portion is staked to a support frame apertured to receive a liquid drop.

The disclosed details of the element of that patent are incorporated herein by reference.

The invention hereinafter described refers to blood serum as the preferred liquid under analysis. In addition, other analyte-containing liquids can be so analyzed, including industrial liquids containing non-biological analytes.

The invention features the use of a removing means that provides relative separation between the test element and reflectometer face previously in contact, prior to relative movement that would cause wear if the separation were not first achieved. Because of this, complicated gearing mechanisms are avoided.

An analyzer such as that illustrated in FIGS. 1-2 comprises a stationary fiber optics reflectometer 20, means 40, FIG. 2, for pressing a loaded test element E' into contact with the reflectometer, and removing means for removing a scanned test element after moving the test element and the scanning head of the reflectometer relative to each other, as described hereinafter. Additionally, the analyzer can include advancing means for moving a test element into the reflectometer, an incubator 100, and means 120 for feeding test elements E to the incubator, FIG. 1.

Figure 2:
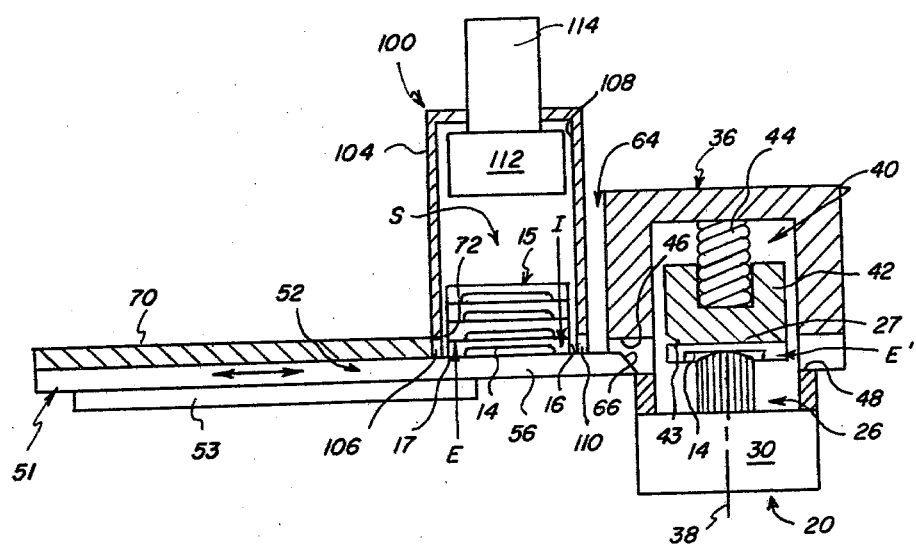
FIG. 2 is a vertical, partly schematic section view taken generally along the plane designated as II-II in FIG. 1.
Figure 3:
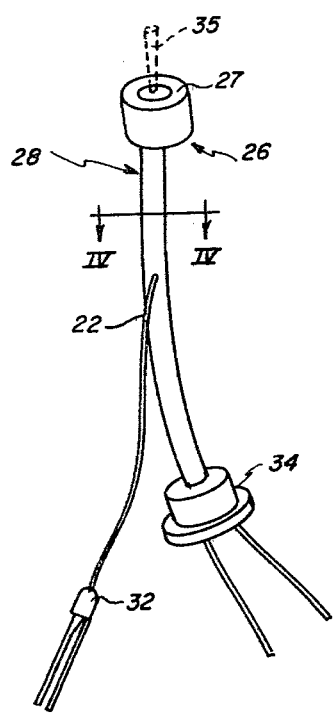
FIG. 3 is an isometric view of the fiber optics head of the reflectometer of the invention.
Figure 4:
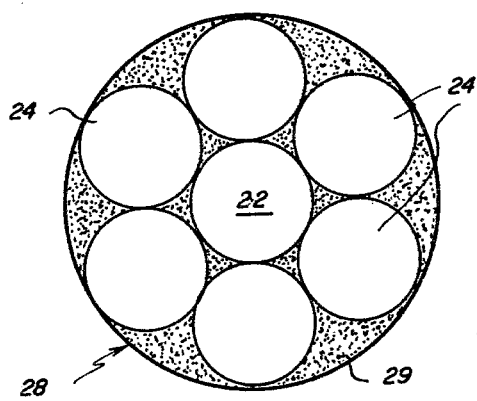
FIG. 4 is a section view taken generally along the line IV-IV of FIG. 3.

The reflectometer 20, FIGS. 2-4, comprises optical fibers at least one of which (22) is a light-emitting optical fiber and a plurality of which (24) are light-collecting fibers, FIG. 4. These are joined together at a stem 28, FIG. 3, to form an optical scanning head 26 that can be flat on its contact face 27, or curved as shown in FIG. 2. Preferably fibers 24 are geometrically positioned around centrally disposed fiber 22 with cladding 29 between them, FIG. 4.

The illumination source and photodetectors for the fibers of stem 28 are conventional, and are preferably housed as a unit 30, FIG. 2. In its simplest form (a single wavelength device), the light-emitting center fiber 22 is coupled to a LED illumination source 32, FIG. 3, having an output at a suitable wavelength. Wavelengths particularly useful with the chemistries described in the above-noted patents include 565, 590, 610, and 700 nm. The light-collecting fibers 24, FIG. 4, are cemented as a bundle to a silicon p.i.n. photodetector 34, FIG. 3, within unit 30. An alternative construction features fiber 22 coupled to an alternate light source, such as a filament lamp, quartz halogen lamp, or xenon flash tube, filtered to the wavelength of interest either at the source or at the photodetector.

When using an LED as source 32, a discontinuous "on-off" mode of operation, e.g., at 20 mA, is a preferred operating procedure. Such discontinuous mode of operation permits more than one light-emitting fiber and illumination source to be included in the scanning head, each source being operated to emit a different wavelength. Such a multiple light-emitting fiber head is preferred if more than one kind of analyte is to be tested.

The readings of the photodetector are conveyed to a conventional data processor, such as a microprocessor, and displayed by a printer or a display screen. The data processor, not shown, preferably includes the capability for calibrating the analyzer.

The angle of reflectance within the fibers 22 and 24 is a characteristic of the fibers chosen, and can be, e.g., about 30°. Such optical fibers are conventional and can be selected from a variety of materials. Highly preferred materials for such fibers include polymethyl methacrylate and polystyrene.

Fiber 22 thus emits a cone of light 35, FIG. 3, into which a test element is placed for detection, as hereinafter described.

A chamber 36 provides a read station in which scanning head 26 projects upwardly, FIG. 2. Center axis 38 of head 26 is thus oriented vertically. Chamber 36 includes means 40 for pressing test element E' into contact with face 27 of head 26, and specifically the transparent support portion 14 of the test element. Means 40 comprises a platen 42 beveled at edge 43 and a biasing element such as a spring 44 under compression.

Chamber 36 further includes an access aperture 46 by which the test elements are introduced, and an exit aperture 48 through which scanned test elements are removed from reflectometer 20. Retaining means such as springs 49, FIGS. 5a and 5c-5f, are preferably mounted in chamber 36 so that they are disposed at both sides of aperture 46 to assist in holding a newly positioned test element in place until platen 42 presses it against head 26, as is described hereinafter. Such springs are mounted above the plane of the slide, as shown, or alternatively are mounted in the plane to project into the path of the slide.

Figure 5A:
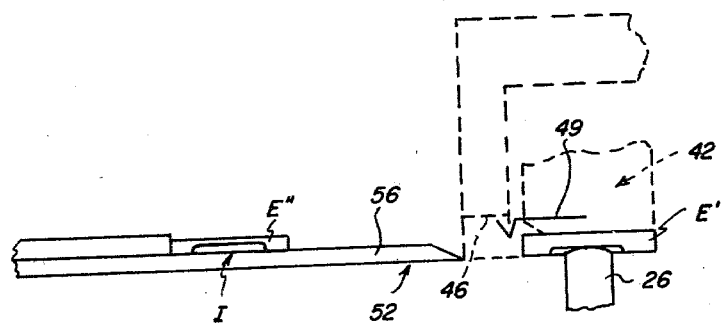
FIGS. 5a-5f are fragmentary schematic elevational views, partly in section with related parts shown in dashed lines, illustrating the sequential steps in the operation of the invention.
Figure 5B:
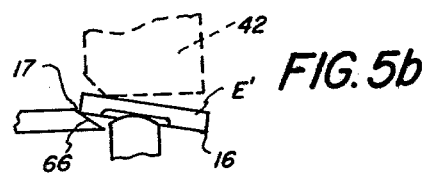
Figure 5C:
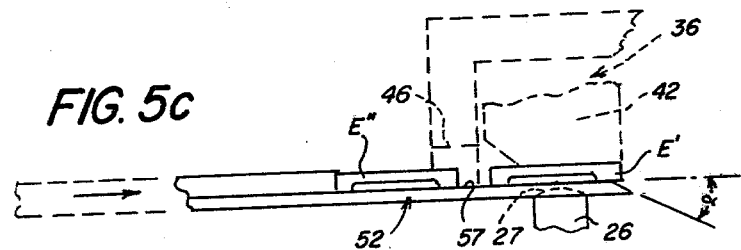
Figure 5D:
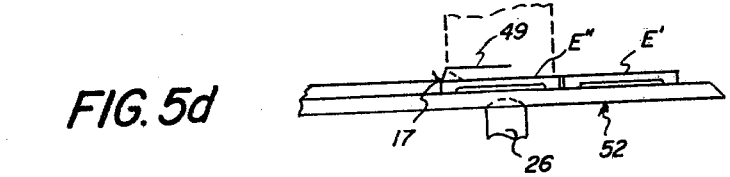
Figure 5E:
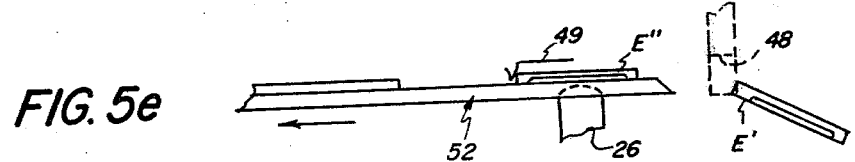
Figure 5F:
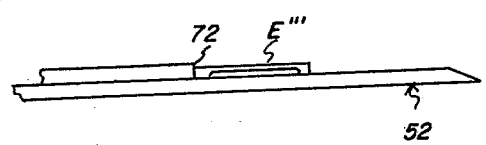
Figure 5F:

In accordance with one aspect of the invention, removing means are provided with means for lifting test element E' off face 27 of the scanning head and for thereafter pushing the element across face 27 and thus out of the reflectometer. Such means includes a pusher element 52 reciprocally mounted on fixed rails 53, FIG. 2. Element 52 is preferably bifurcated to form two arms 54 and 56, FIG. 1. The arms are spaced sufficiently to straddle scanning head 26, when advanced. Arms 54 and 56 have an upper supporting surface 57, FIG. 1, which, when advanced as shown in FIG. 5c, is located above face 27 of scanning head 26. One end 51 of pusher element arm 54 is provided on its exterior surface with a rack gear 58, FIG. 1. This is engaged by a pinion gear 60 driven by a conventional stepping motor 62, such as a Berger/Lahr stepping motor.

At opposite end 64 of pusher element 52, a camming surface 66, FIG. 2, is provided on arms 54 and 56. Surface 66 has a bevel angle α, FIG. 5c, which, is sufficient to lift off a scanned test element against the pressure of means 40, as described hereinafter. Preferred values of this angle are between about 15 and 60 degrees, most preferably about 20 degrees.

Arms 54 and 56 slide into and through aperture 46 from a starting position in which camming surfaces 66 are free of contact with the test element within the reflectometer. As is described hereinafter, surfaces 66 move forward to lift the scanned element E' off face 27 and out aperture 48.

To move a test element E into chamber 36, advancing means are preferably included. Most preferably, the advancing means comprises pusher element 52 described above as the removing means, and plate 70 connecting arms 54 and 56. The plate has a forward edge 72, FIG. 1, that forms a raised shoulder that extends from arm 54 to arm 56. The height of edge 72 is selected so that it is slightly less than the thickness of one test element resting on arms 54 and 56 at position I, FIG. 2. In this fashion, edge 72 of plate 70 engages a rested test element at its trailing edge 17, and pushes the element into the reflectometer synchronously with the removal of the element just read.

It will be appreciated that the above-described analyzer is useful to scan the test elements by loading them one at a time at position I on arms 54 and 56, and by pushing them into chamber 36. Although this can be done without the use of storage facilities, such as by hand loading, a preferred construction is one in which a plurality of sample-containing test elements are stored in a stack S adjacent reflectometer 20, above pusher element 52. To this end, an incubator 100 comprising a container 102, FIG. 1, is mounted adjacent to chamber 36. One of the walls 104, FIG. 2, of container 102 includes aperture 106 sized to allow edge 72 of pusher element 52 to enter and engage only the bottommost test element of the stack. The opposite container wall 108 has an outlet aperture 110 adapted to permit such bottommost element to be transferred into reflectometer 20 as edge 72 of the pusher element urges it along.

To cover the stack and to urge the test elements downwardly, a platen 112 is included, along with a handle 114. Platen 112 is also useful to heat the test elements, either passively or actively, and conventional heating elements for incubator 100 are optionally disposed at appropriate locations. If the test elements E are loaded into the stack by hand, then handle 114 is preferably raised manually.

Most preferably, however, test elements are inserted into incubator 100 by feeder means 120, FIG. 1. Means 120 comprises a sliding pusher 122 mounted on a track comprising two rails 124. A test element support surface 126 is provided between rails 124. Feeder means 120 cooperates with an aperture 128 in incubator 100 to allow the insertion of test elements, arrows 129, onto the top of the stack S. A handle 130 allows pusher 122 to be manually operated in conjunction with the manual raising of handle 114 of the platen. Alternatively, the two handles are mechanically or electronically linked together, not shown, to cause platen 112 to rise automatically as pusher 122 is advanced toward aperture 128.

The operation of the analyzer will be apparent from the preceding description. The operation of pusher element 52 is illustrated in FIGS. 5a-5f. Test element E' is scanned while it is pressed by platen 42 into contact with scanning head 26, FIG. 5a. A second test element E", yet to be scanned, is in position I on pusher element 52, such as by being the bottommost element in stack S, FIG. 2. As pusher element 52 is advanced into aperture 46 from its starting position, FIG. 5a, camming surfaces 66 lift element E' off scanning head 26 against the downward urging of platen 42, FIG. 5b, first by lifting trailing edge 17 in a direction generally aligned with the center axis of head 26. Thereafter, leading edge 16 of the element is raised and at the same time, second element E" is carried part-way into aperture 46 of chamber 36, FIG. 5c. At this point, scanned element E' no longer contacts face 27. As the second element E" is pushed by edge 72, it pushes element E' out from under platen 42, FIG. 5d. Retaining springs 49 slide over test element E" and slip into place behind trailing edge 17 thereof. Pusher element 52 is now in its advanced position. During movement of elements E' and E" into and out of contact with platen 42, neither test element is in contact with scanning head 26. Therefore, movement of the test elements perpendicularly to the center axis of head 26 does not create wear on the head.

Thereafter, pusher element 52 is returned to its starting position. At this time, test element E' is kept from returning by the action of retaining spring 49. As the pusher element is returned, test element E' is pushed out aperture 48 by test element E", FIG. 5e. After pusher element 52 clears spring 49, FIG. 5f, test element E" is pressed into contact with face 27 of scanning head 26. The contact is made in the reverse order of lift-off of FIG. 5b: first the leading portion of the test element is let down and then the trailing portion. A third test element E''' is then positioned in front of edge 72, and the cycle is repeated.

Alternatively, a useful analyzer is one in which the reflectometer, rather than the platen, is movable, with the platen being fixed (not shown). In such an embodiment, springs bias the reflectometer against the platen, and camming surface 66 is rotated 90° so that it bears against reflectometer face 27 to cam it downwardly, prior to lateral movement of the test element across face 27.

The resulting analyzer described above is particularly advantageous because of its relative simplicity. Such analyzers are particularly useful for small scale analysis, such as in doctors' offices.

The invention has been described in detail with particular reference to preferred embodiments thereof, but it will be understood that variations and modifications can be effected within the spirit and scope of the invention.

What is claimed is:

1. In an analyzer for measuring an analyte in a liquid by scanning a test element containing the liquid, said analyzer including a reflectometer having a face adapted to contact a test element during scanning and means for biasing the test element and said reflectometer face into contact with each other while the element is being scanned, the improvement comprising removing means for removing a scanned test element from said reflectometer, said removing means including first means for moving said scanned element and said face out of contact with each other, and second means for pushing said element across said face, said first means and said second means being configured and arranged so that said second means is operative only after said first means is operative.

2. An analyzer as defined in claim 1, wherein said reflectometer includes an optical scanning head having a center axis, and wherein said removing means includes a pusher element and means for moving said pusher element in a direction that is generally perpendicular to said scanning head axis, said pusher element including a camming surface for forcing the scanned test element to move away from said scanning head in a direction that is generally aligned with said axis.

3. An analyzer as defined in claim 2, wherein said pusher element is mounted and constructed to move between a starting position wherein a test element in contact with said scanning head is free of contact with said pusher element, and an advanced position wherein said pusher element is under the scanned test element and astraddle said scanning head.

4. An analyzer as defined in claim 2, and further including means for supplying said test elements in a stack adjacent said reflectometer and above said pusher element, said pusher element including a raised shoulder dimensioned to engage the bottommost element of said stack.

5. An analyzer as defined in claim 1, wherein said removing means comprises a bifurcated pusher element having said camming surface mounted on an end thereof.

6. An analyzer as defined in claim 5, wherein said camming surface is beveled at an angle sufficient to lift a test element off said reflectometer and onto said bifurcated element as said bifurcated element is advanced toward said reflectometer.

7. An analyzer as defined in claim 1, and further including means for supplying said test elements in a stack adjacent said reflectometer.

8. An analyzer as defined in claim 7, and further including advancing means for moving a test element into a position within said reflectometer, said advancing means being disposed below said stack and including ejector means for removing the bottommost one of said stack of test elements.

9. An analyzer as defined in claim 8, wherein said ejector means comprises a raised shoulder on said advancing means dimensioned to engage the trailing edge of said bottommost stack element only.

10. An analyzer as defined in claim 1, and further including advancing means for moving a test element into a position within said reflectometer, means for reciprocating said advancing means between a starting position outside said reflectometer and said position within said reflectometer, and means for retaining a test element moved into said reflectometer while said advancing means is moved back to said starting position.

11. An analyzer for measuring an analyte in a liquid by scanning a test element containing the liquid, said analyzer including a reflectometer adapted to contact a test element during scanning, advancing means for moving a test element into scanning position within said reflectometer, means for pressing the test element into contact with said reflectometer while the element is being scanned, and removing means for removing a scanned test element from said reflectometer, said removing means being provided with a camming surface at one end thereof, said camming surface being beveled at an angle sufficient to lift a test element off said scanning head and onto said removing means as said camming surface is advanced toward said scanning head, said advancing means and said removing means being coupled for synchronous movement.

12. An analyzer as defined in claim 11, wherein said advancing means and said removing means together comprise a bifurcated element.

13. An analyzer as defined in claim 12, and further including means for supplying said test elements in a stack adjacent said reflectometer above said bifurcated element, said bifurcated element including a raised shoulder dimensioned to engage the bottommost one of said stack of test elements.

14. An analyzer as defined in claim 12, and further including means for reciprocating said bifurcated element between a starting position outside said reflectometer and said position within said reflectometer, and means for retaining a test element moved into said reflectometer while said bifurcated element is moved back to said starting position.

* * * * *

UNITED STATES PATENT AND TRADEMARK OFFICE
CERTIFICATE OF CORRECTION

PATENT NO. : 4,302,420
DATED : November 24, 1981
INVENTOR(S) : R. F. Jakubowicz, P. N. Schnipelsky It is certified that error appears in the above-identified patent and that said Letters Patent are hereby corrected as shown below:

In Fig. 1, the numeral "20" on the left-hand side of the drawing, for which the arrow points to a rectangular plate, should read --70--.

In Fig. 2, the lead line for numeral 27 should extend through the test element E to the top of head 26.

In column 4, line 17, delete "5c" and insert --5d--.

In column 4, line 64, delete the word --rested--.

Signed and Sealed this

Thirteenth Day of November 1984

[SEAL]

Attest:

GERALD J. MOSSINGHOFF

Attesting Officer

Commissioner of Patents and Trademarks